United States Patent [19]

Pesnelle et al.

[11] 4,124,648
[45] Nov. 7, 1978

[54] PROCESS FOR THE PREPARATION OF NORPATCHOULENOL AND INTERMEDIATES THEREFOR

[75] Inventors: Pierre Pesnelle, Le Cannet; Paul J. Teisseire, Grasse, both of France

[73] Assignee: Societe Anonyme des Etablissements Roure-Bertrand Fils & Justin Dupont, Paris, France

[21] Appl. No.: 444,488

[22] Filed: Feb. 21, 1974

[30] Foreign Application Priority Data

Feb. 28, 1973 [CH] Switzerland .................... 2885/73

[51] Int. Cl.$^2$ ........................................... C07C 29/00
[52] U.S. Cl. ................................................. 568/817
[58] Field of Search .................................. 260/617 F

[56] References Cited

U.S. PATENT DOCUMENTS 3,673,261  5/1972  Kretschmar et al. ............ 260/617 F

OTHER PUBLICATIONS

Buchli et al., "Constitution of Patchouli Alcohol and Absolute Configuration of Cedrene," J. Am. Chem. Soc., 83, 927–938 (1961).
Buchli, "Synthesis of Patchouli Alcohol," J. Am. Chem. Soc., 84, pp. 3205–3206 (1962).
Dobler et al., "The Structure of Patchouli Alcohol," Proc. Chem. Soc. (London), p. 383 (1963).
Buchli et al., "Synthesis of Patchouli Alcohol," J. Am. Chem. Soc. 86, pp. 4438–4444 (1964).
Hickinbottom, Reactions of Organic Compounds, pp. 138–143, (1957).
House, Modern Synthetic Reactions, pp. 11–12, (1972).
Reagents For Organic Synthesis, Fieser et al., (1967) pp. 46–47.

Primary Examiner—James O. Thomas, Jr.
Assistant Examiner—James H. Reamer
Attorney, Agent, or Firm—Wallenstein, Spangenberg, Hattis & Strampel

[57] ABSTRACT

A process for the preparation of norpatchoulenol is described according to the reaction scheme:

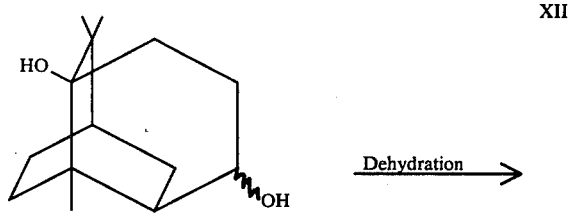

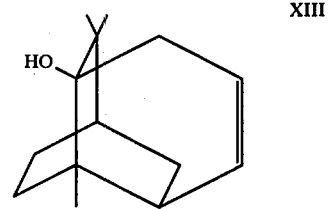

Novel intermediates of formulae

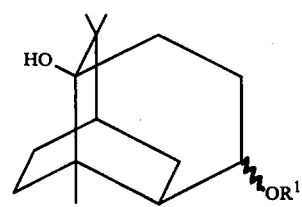

wherein R$^1$ is methyl or benzyl and

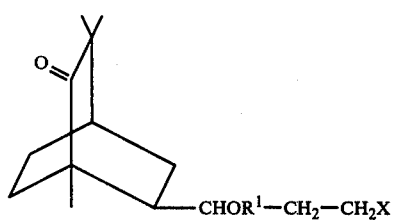

wherein R$^1$ is methyl or benzyl and X is hydroxy, trityloxy, tosyloxy or halogen, are also described.

2 Claims, No Drawings

PROCESS FOR THE PREPARATION OF NORPATCHOULENOL AND INTERMEDIATES THEREFOR

DETAILED DESCRIPTION OF THE INVENTION

This invention relates to a process for the manufacture of norpatchoulenol.

Norpatchoulenol is an unsaturated tricyclic alcohol of the formula

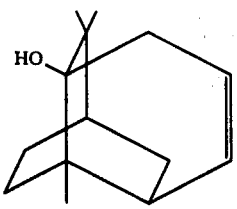

XIII present in patchouli oil and having a highly characteristic odour.

No synthesis of this alcohol, which is also sometimes known as nordehydropatchoulol, has so far been described.

A process for the production of norpatchoulenol has now been found. This process comprises dehydrating a glycol of the formula

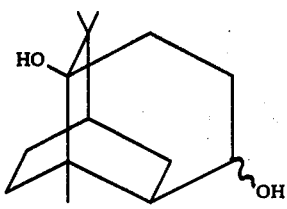

XII

The glycol of the formula XII may be prepared by ether cleavage, especially by hydrogenolysis, from a monoether of the glycol XII. Ethers which may be used include those where the secondary OH group of norpatchoulenol is etherified with a readily cleavable group such as benzyl. A suitable precursor for the production of the glycol XII is thus, for example, the benzyl ether of the formula

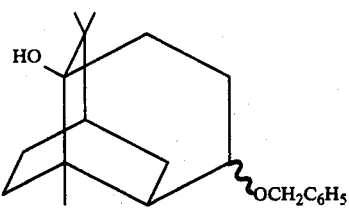

XI b which can be hydrogenolysed using conventional methods.

The benzyl ether XI b and the corresponding methyl ether, that is the compounds of the general formula

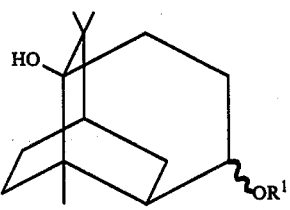

XI wherein $R^1$ signifies methyl or benzyl, are novel and thus constitute a further aspect of the invention.

The following reaction scheme shows how the new monoethers of the general formula XI may, be prepared.

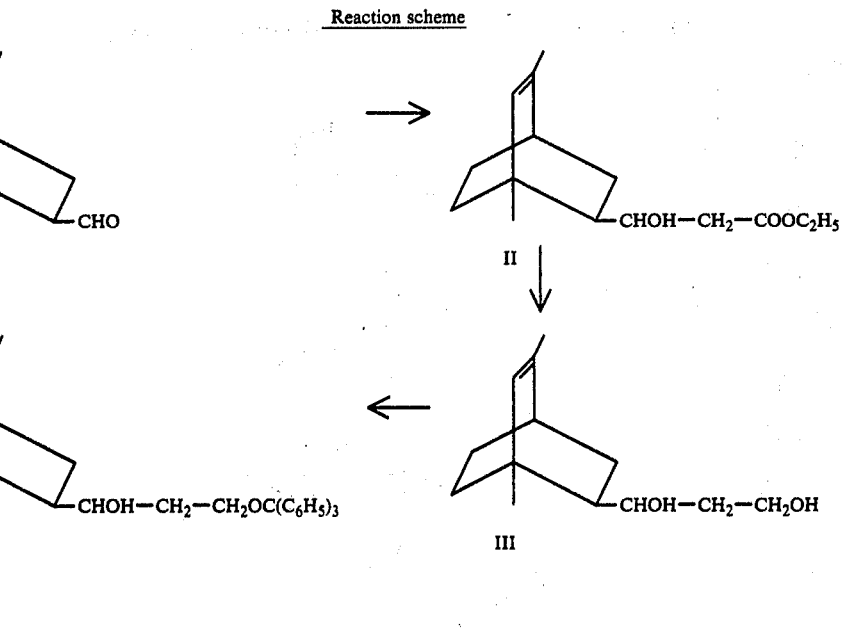

Reaction scheme

-continued
Reaction scheme
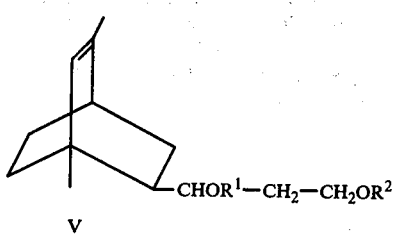
V
| R¹ | R² |
|---|---|
| Va: —CH₃ | —C(C₆H₅)₃ |
| Vb: —CH₂C₆H₅ | —C(C₆H₅)₃ |
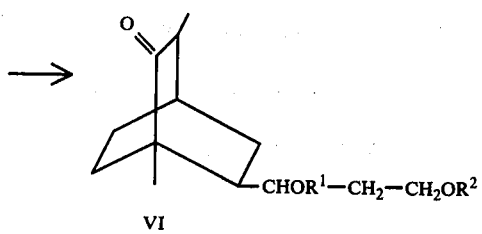
VI
| R¹ | R² |
|---|---|
| VIa: —CH₃ | —C(C₆H₅)₃ |
| VIb: —CH₂C₆H₅ | —C(C₆H₅)₃ |
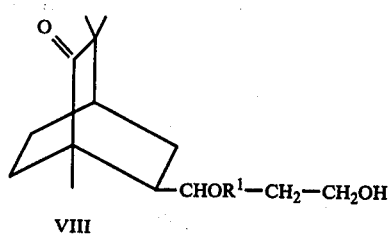
VIII
| VIIIa: R¹ = —CH₃ |
| VIIIb: R¹ = —CH₂C₆H₅ |
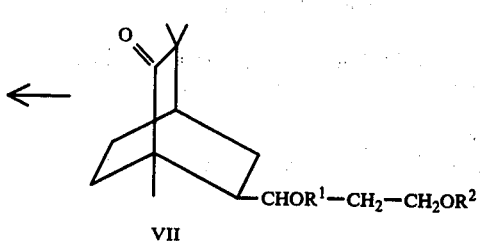
VII
| R¹ | R² |
|---|---|
| VIIa: —CH₃ | —C(C₆H₅)₃ |
| VIIb: —CH₂C₆H₅ | —C(C₆H₅)₃ |
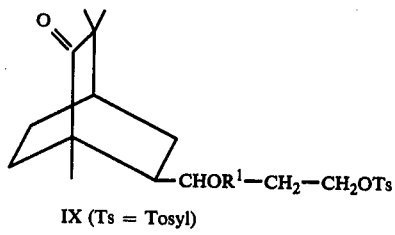
IX (Ts = Tosyl)
| IXa: R¹ = —CH₃ |
| IXb: R¹ = —CH₂C₆H₅ |
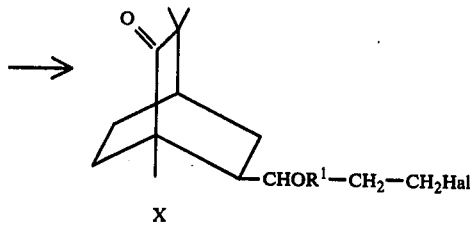
X
| R¹ | Hal |
|---|---|
| Xa: —CH₃ | I |
| Xb: —CH₂C₆H₅ | I |
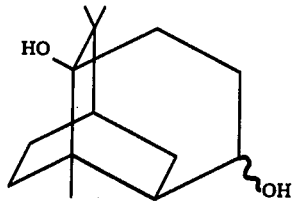
XII
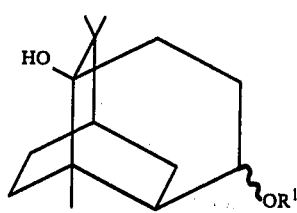
XI

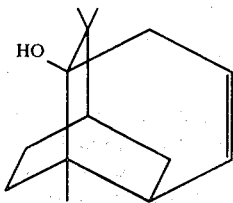

XIII

| XIa: R¹ = —CH₃ |
| XIb: R¹ = —CH₂C₆H₅ |

-continued
Reaction scheme

The synthesis takes as its starting point the unsaturated bicyclic aldehyde I, which can be obtained according to J.Org.Chem. 37 (1972), 2871. Treatment of this aldehyde I with ethyl bromacetate in the presence of zinc according to the Reformatsky reaction yields the ester II (as a diastereomeric mixture), whose ester group can be reduced to a primary alcohol group by means of LiAlH₄. By recrystallization from petroleum ether, there can be obtained from the so obtained mixture of the two diastereomeric glycols III, one is in the crystalline form m.p. 113–114° C. The reactions described below are based on this isomer.

First, the primary OH group of the alcohol III is etherified using triphenylchloromethane. The secondary OH group of the so obtained trityl ether IV is then etherified. By methylation, there is thus obtained the methyl trityl ether V a and, by benzylation, the benzyl trityl ether V b.

By hydroboronation and oxidation, the compounds of the formula V can be converted into the corresponding ketones of the formula VI and the latter can be converted by methylation into the compounds of the formula VII. From these, there are obtained, after hydrogenolysis or hydrolytic cleavage of the trityl group, the free primary alcohols of the formula VIII. Via the tosylate of the formula IX, there are then attained the halides X (wherein "Hal" may be iodine, chlorine or bromine) which, after cyclisation, finally yield the tricyclic momoethers of the formula XI.

The invention will now be illustrated with reference to the following Examples.

EXAMPLE 1

(a) To a 100 ml flask there are added 3.3 g (15 mmol) of the diol III, 6 g of trityl chloride (21 mmol), 50 ml of anhydrous benzene and 3 ml of pyridine. The mixture is held for 2 hours under reflux. After cooling, the precipitated pyridine chloride is filtered off, the solvent distilled off and the residue taken up in a petroleum ether/ether mixture (8:2). After filtration over 100 g neutral Al₂O₃ of activity 1, there are obtained 4 g of the trityl monether IV IR: 3500, 3090, 3060, 1600, 1490, 1070, 705 and 760 cm⁻¹

NMR 1.10, 1.70, ~3-4, 5.36.

(b) To a flask provided with a stirrer, there are added 5.9 g (13 mmol) of trityl monoether IV, 60 ml of glyme, 2 g (14 mmol) of methyl iodide and then 0.8 g of sodium hydride (50%, 15 mmol) are added in small portions. The mixture is then heated over 2 hours to reflux, there are successively added a further 2 g of methyl iodide and 0.5 g of sodium hydride, whereupon the reaction is terminated after a further 2 hours. The reaction mixture is mixed with 100 ml of ether and then with 5 ml of water. The ethereal solution is then washed with saturated NaCl solution until neutral. The solution is dried over sodium sulphate and the solvent distilled off. There are thus obtained 7.4 g of crude diether V a, which is purified by chromatography over 100 g of neutral aluminium oxide. The yield of thin-layer chromatographically homogeneous diether V a amounts to 6.65 g.

IR: 3030, 3060, 3020, 2820, 1600, 1495, 1070, 1095 700, 745, 1650 cm⁻¹

NMR: 1.14, 1.72, 3.01, 5.42~7.20

(c) 1 g of the diether V a, dissolved in 15 ml of tetrahydrofuran, is treated at 0° C. with a stream of diborane (B₂H₆). The reaction is followed by thin-layer chromatography. After disappearance of the starting material, several drops of water are added and the mixture is then poured into 20 ml of water. The mixture is then extracted with 4 times 10 ml of benzene, washed with 2 times 10 ml of saturated NaCl solution, dried over sodium sulphate and the solvent distilled off. There are obtained 1.1 g of crude borane. For the oxidation of the obtained borane, this crude borane is dissolved in 15 ml of pyridine and the solution added to a solution of 1.6 g of CrO₃ in 16 ml of pyridine. The mixture is stirred overnight at room temperature, poured into 60 ml of ether and the precipitate filtered off and washed with ether. The organic phase is washed with 10% cold hydrochloric acid until neutral. After drying and distillation off of the ether, there are obtained 1.1 g of crude ketone VI a. After chromatography over 25 g of neutral aluminium oxide (elution with petroleum ether/ether 8:2), 200 mg of ketone VI a are obtained with the following spectral data:

IR: 3080, 3060, 3020, 2820, 1710, 1595, 1490, 1080, 705, 750, 760 cm⁻¹

(d) Manufacture of trityl potassium: 100 mg of potassium cut up into fine segments are added to a solution of 600 mg pf triphenylmethane in 5 ml of glyme. The mixture is stirred at room temperature under an inert atmosphere for 16 hours.

Alkylation: To a 25 flask provided with a stirrer there is added a solution of 200 mg of the ketone VI a in 5 ml of glyme and a sufficient amount of trityl potassium. If the red colouration remains, the mixture is stirred for 20 minutes and then mixed with 0.5 ml of methyl iodide. After 6 hours at room temperature, the reaction mixture is poured into 25 ml of water and then extracted with 3 times 20 ml of ether. The extracts are washed with water and then with saturated NaCl solution. After drying over sodium sulphate, the solvent is evaporated. After chromatography of the crude product through 50 g of neutral aluminium oxide, there are obtained 25 mg of methylated ketone VII a as well as 100 mg of the starting material.

IR: 3080, 3060, 3020, 1710, 1595, 1485, 1075, 1060, 2820, 770, 760, 750, 1380, 1375 cm$^{-1}$
NMR: 0.95, 1.04, 1.08, 3.08, 3.36, 7.26

(e) A solution of 1.45 g of crude ketone VII a in 100 ml of ethanol is treated with hydrogen in the presence of 0.25 g of palladium on carbon (5%). The hydrogenolysis is continued for 17 hours. After filtration of the catalyst, the solvent is distilled and the residue chromatographed through a column of 40 g of silica gel. Elution with a petroleum ether/ether mixture (3:7) produces 125 mg of the alcohol VIII a.
IR: 3320, 2820, 1705, 1085 cm$^{-1}$
NMR: 0.86, 1.08, 3.32

(f) 101 mg of the alcohol VIII a are dissolved in 9 ml of pyridine. The mixture is cooled to $-12°$ C. and 300 mg of tosyl chloride added. The mixture is left to stand for 14 hours at ca. $-14°$ C.; then the reaction mixture is poured into 50 ml of 10% hydrochloric acid and extracted with ether (3 times 20 ml). The organic phase is washed with 10% hydrochloric acid and then with aqueous sodium bicarbonate solution. The obtained tosylate IX a (100 mg) does not need to be purified for the subsequent reaction.

(g) 100 mg of the so obtained tosylate IX a, dissolved in 15 ml of acetone, are treated for 20 hours at room temperature with 300 mg of NaI. The reaction mixture is poured into 30 ml of water and then extracted with 3 times 15 ml of ether. After washing with water and drying over sodium sulphate, the solvent is evaporated off. There are obtained 87 mg of crude iodide X a, which is chromatographed through 6 g of neutral aluminum oxide. Elution with a petroleum ether/ether mixture 8:2 produces 68 mg of iodide X a.

(h) To a 10 ml flask there are added 68 mg of iodide X a, dissolved in 5 ml of tetrahydrofuran, and then 100 mg of finely divided sodium. The mixture is stirred for 4 hours under reflux, then cooled to room temperature, the solvent removed and the sodium washed with tetrahydrofuran. There is added 1 ml of water and the mixture is acidified with 10% hydrochloric acid. After the addition of 25 ml of ether, the mixture is decanted, washed with bicarbonate solution and dried over sodium sulphate. After evaporation of the solvent, there are obtained 44 mg of crude cyclisation product XI a. Chromatography through a column of 5 g of silica gel and elution with a petroleum ether/ether mixture 8:2 yield 17 mg of cyclisation product XI a.
IR: 3460, 2820, 1085 cm$^{-1}$
NMR: 0.78, 1.02, 1.07, 3.18
Mass spectrum: 238, 220, 206, 195, 191, 188, 177, 163, 145, 109, 93, 81, 69, 55.

EXAMPLE 2

By analogy with the process of Example 1b there is obtained from the trityl monoether IV by reaction with benzyl chloride (c.f. Canad. J. of Chem. 44 (1966), 1591) the diether V b with the following spectral data:
IR: 3060, 3020, 1600, 1490, 1090, 1070, 700, 745 cm$^{-1}$
NMR: 1.11, 1.72~2.18~2.75 4.28 5.42

The oxidation of the obtained diether V b according to Example 1 c leads to the ketone VI b, which can be methylated to the compound VII b by analogy with the process of Example 1 d. After selective cleavage of the trityl group, with acetic acid in homogeneous ethereal phase at room temperature (c.f. e.g. J. Chem. Soc. 1956, 3459) the obtained monoether VIII b is converted into the tosylate IX b (by analogy with the process of Example 1 f); this is converted into the iodide X b (according to the process of Example 1 g), whereupon finally the cyclisation (according to Example 1 h) leads to the tricyclic benzyl ether XI b. Its hydrogenolysis to the free diol XII can be carried out according to conventional methods of hydrogenolytic benzyl ether cleavage.

The dehydration of the diol XII to norpatchoulenol XIII can be undertaken as described as follows with reference to a diol XII having the S configuration of the carbon carrying the secondary OH group:

400 mg of the above mentioned diol in 1 ml of pyridine are mixed with a solution of 500 mg (2.06 mmol) of p-bromo-benzenesulphonyl chloride in 1 ml of pyridine. The mixture is stirred for 1.5 hours at 0° C., then poured onto ice and extracted with ether. After extraction, washing to neutrality, drying and distillation of the ether, there are obtained 300 mg of a light yellowish crystallised product, which is chromatographed through a column of 10 g of silica gel. Elution with a petroleum ether/ether mixture (9:1) yields firstly 110 mg of a crystalline mixture of 2 products, with norpatchoulenol XIII as the main product. Further elution with petroleum ether/ether mixture 7:3 yields 160 mg of unreacted diol XII. Melting point of the thus obtained pure norpatchoulenol: 180°–183° C.

We claim:
1. A process for the preparation of norpatchoulenol, which comprises dehydrating a glycol of the formula

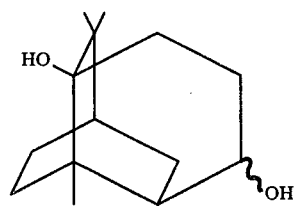

XII

2. A process as claimed in claim 1 wherein the glycol of the formula XII is prepared by hydrogenolysis of an ether of the formula

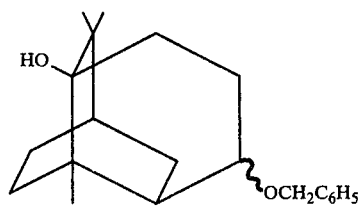

XI b

* * * * *